United States Patent [19]

Burgess et al.

[11] Patent Number: 4,668,193
[45] Date of Patent: May 26, 1987

[54] DENTAL CROWN COMPOSITE AND METHOD OF MAKING AND USING SAME

[75] Inventors: Lester E. Burgess, Swarthmore; Joe J. Capista, Jr., Media, both of Pa.

[73] Assignee: White Cap Dental Company, Inc., Springfield, Pa.

[21] Appl. No.: 687,643

[22] Filed: Dec. 31, 1984

[51] Int. Cl.⁴ .............................................. A61C 5/08
[52] U.S. Cl. .................. 433/222.1; 433/159; 433/218; 433/223
[58] Field of Search .............. 433/222, 223, 218, 219, 433/208, 159

[56] References Cited

U.S. PATENT DOCUMENTS

| | | | |
|---|---|---|---|
| 888,297 | 5/1908 | Bell | 433/159 |
| T954,010 | 1/1977 | Brunner et al. | 427/335 |
| 1,609,549 | 12/1926 | Jaques, Jr. | 433/218 |
| 3,079,361 | 2/1963 | Plueddemann | 269/40 |
| 3,265,202 | 8/1966 | Cornell | 206/63.5 |
| 3,375,582 | 4/1968 | Myerson | 433/223 |
| 3,423,830 | 1/1969 | Halpern et al. | 523/115 |
| 3,423,831 | 1/1969 | Semmelman | 433/212.1 |
| 3,488,846 | 1/1970 | Cornell | 433/203.1 |
| 3,508,983 | 4/1970 | Origer et al. | 156/3 |
| 3,522,075 | 7/1970 | Kiel | 117/72 |
| 3,644,166 | 2/1972 | Gause | 161/89 |
| 4,028,325 | 6/1977 | King et al. | 260/42.15 |
| 4,052,524 | 10/1977 | Harakas et al. | 428/383 |
| 4,069,360 | 1/1978 | Yanagisawa et al. | 428/64 |
| 4,103,045 | 7/1978 | Lesaicherre et al. | 427/82 |
| 4,118,540 | 10/1978 | Amort et al. | 428/447 |
| 4,292,236 | 9/1981 | Ibsen et al. | 264/36 |
| 4,332,564 | 6/1982 | Lord | 433/223 |
| 4,364,731 | 12/1982 | Norling et al. | 433/218 |
| 4,398,007 | 8/1983 | Kubota et al. | 526/273 |
| 4,433,959 | 2/1984 | Faunce | 433/222 |
| 4,478,579 | 10/1984 | Fischer et al. | 433/222.1 |

FOREIGN PATENT DOCUMENTS

510893  8/1938  United Kingdom .............. 433/222

*Primary Examiner*—John J. Wilson

[57] ABSTRACT

An improved dental crown veneer composite which has excellent appearance and wear characteristics and which can be installed in a single office visit is disclosed. Also described is a method of installation, a method of producing said dental crown composite and useful tools for practicing the invention.

20 Claims, 6 Drawing Figures

DENTAL CROWN COMPOSITE AND METHOD OF MAKING AND USING SAME

BACKGROUND OF THE INVENTION

Heretofore, the restoration of posterior teeth, exhibiting decay, erosion, or fracture, has involved techniques such as fitting stainless steel crowns or caps over the damaged teeth. While the stainless steel crowns are well suited for structural and functional restoration of these teeth, and suit the expense capability of the lower income group of dental patients, they are unaesthetic. Another low cost alternative which is more aesthetic is the polycarbonate resin crown. This crown is not favored because such a crown exhibits poor wear resistance, inadequate retention, and is susceptible to cracking in service. It is therefore a desirable approach to the restoration of teeth to combine the functional properties of a stainless steel crown with the aesthetics presented by the polymeric crowns. One such approach which has been suggested is to veneer the steel crown with a thin layer of polymeric resin. This option, which still would provide an economical cost to the lower income dental patient, would combine the reliable function of the stainless steel dental crown and offer the normal appearance of a porcelain or plastic crown. Although low cost veneering has been employed for a number of years for the restoration of natural teeth, to mask defects such as developmental anomalies and tetracycline and fluorosis stains, a durable stainless steel-polymer veneer approach has not been developed.

In veneering natural teeth, the damaged teeth are isolated, cleaned, etched with phosphoric acid, and dried. A composite restorative resin is applied to the etched surface and cured. Adhesive interlocking of the resin with the etched surface of the tooth enamel results in a bond strength which is sufficient to accomplish a restoration having acceptable clinical durability. Unfortunately, stainless steel is not amenable to a similar approach because retentive etch pits cannot be adequately developed in stainless steel by acid etching as is normally used in natural teeth veneering.

Alternative approaches to produce a durable stainless steel-polymer veneer crown have involved chemical bonding techniques. The widely-used industrial adhesive agents, such as epoxy resins, phenol-formaldehyde resins, and acrylic and other dental approved resins have been employed in the past to adhere polymers to substrates. Unfortunately, the bond formed between the substrate and the polymer provides a weak structural interface relative to the structural stresses presented to the crowns when in service. Not only are the veneered products subject to cracking, flaking, and fracture, the veneer composite may exhibit undesirable permeability to gases such as water vapor, and liquids, thereby allowing further weakening of the veneer structure.

Other approaches to combine functional strength and aesthetics include pigmenting the steel crowns. For example, commercial crowns were at one time available with white pigmented layers. These crowns, however, were not successful because of the rapid loss of the pigment coating after oral placement.

U.S. Pat. No. 4,364,731 describes a more recent attempt to produce an aesthetic-functional composite which involves the procedure of providing a polymeric veneer over a stainless steel crown by applying an intermediate layer of inorganic oxide onto the cleaned stainless steel crown and then applying a layer of silane coupling agent over the inorganic oxide layer and then finally adhering the polymeric veneer to said silane coupling agent layer. This system, however, requires the elaborate time-consuming and generally more costly procedures of two intermediate layers between the stainless steel crown and the polymeric veneer. In addition, the use of silane materials is undesirable because they are generally considered toxic.

As can be appreciated from the foregoing, the need still remains for a dental crown which combines the structural strength of steel and the aesthetics of a polymer resin coating, without the necessity of expensive procedures and toxic chemicals to meet the demand of constant oral exposure. It is therefore a feature of the present invention to provide a dental crown composite, a method of making said dental crown composite, and of applying said dental crown composite which provides a stainless steel polymeric veneered dental crown having strong adhesive bonds between the substrate and the polymer resin and in addition may be installed in a single office visit.

SUMMARY OF THE INVENTION

According to the present invention, a dental crown composite is provided, comprising a dental crown or preformed stainless steel substrate having a formed face suitable for retaining a veneer coating and a veneer coating of an acrylic material or other dental approved resin system chemically bonded within said formed face on said dental crown. As hereinabove and hereinafter described, the term dental crown is understood to mean stainless steel crowns and crowns of other dental approved alloys.

In a preferred embodiment of the present invention, the dental crown composite comprises a metal dental crown substrate having a phosphate layer applied thereto and then having a veneer comprising an acrylic material which is chemically bonded to said phosphate layer on said metallic dental crown substrate.

Also provided is a method for installing the novel dental crown composite of this invention comprising the steps of surgically stabilizing the tooth receiving the dental crown, shaping the tooth stub, selecting the proper size dental crown substrate, forming the formed face in said dental crown substrate while providing holes in a configuration which offers maximum retention strength, shaping said dental crown substrate to fit the tooth stub and the mouth, electroetching said formed face of said dental crown substrate, applying the acrylic material veneer to said formed face of said dental crown substrate thereby creating an acrylic veneer crown composite fitting said tooth stub, and cementing said dental crown composite to said shaped tooth stub.

Another part of the invention herein comprises an electrolytic etching device, for etching the metallic dental crown substrate and producing the phosphate layer, thereon comprising a DC power supply having a positive and a negative terminal, an electrolytic cell having a positive electrode and a negative electrode connected to said positive and negative terminals of said power supply, a phosphate-containing electrolyte within a special electrolytic cell which, because of its shape and small volumetric configuration, promotes high temperature phosphatizing of said substrate and electrically connecting the positive and negative electrodes, a pair of dental crown substrate holders (one is used for convenience to form a profiled cathodic electrode, but a suitable shaped stainless steel cathode would serve equally well) in said electrolytic cell, one holder located at each electrode, and a retaining means in conjunction with each holder electrically connected to the positive anode and negative cathode electrode respectively which maintain the proper registration of the desired formed face of the dental crown substrate thereby completing the electrical circuit.

Another part of the invention comprises the necessary tools used for mechanically shaping the dental crown formed face and making the preferred holes.

Other embodiments of the present invention will become apparent to those skilled in the art upon a study of the following specification, appended claims, and accompanying drawings.

DETAILED DESCRIPTION OF THE DRAWINGS

Figure 1:
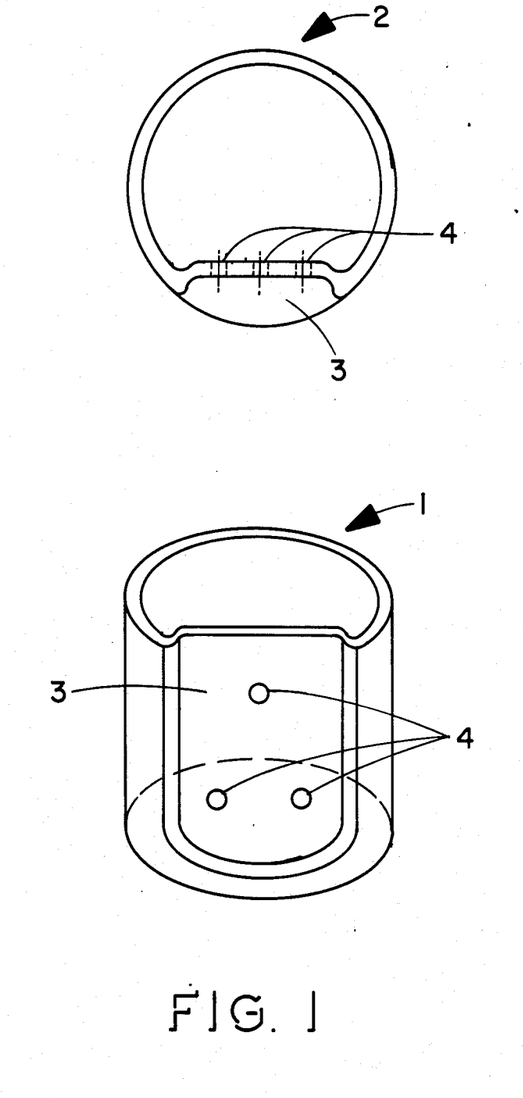
FIG. 1 shows a plan view and top view of a dental crown substrate which has had a perforated formed face produced therein.

FIG. 1 shows a plan view (1) and a top view (2) of a preferred configuration of a preformed dental crown with a formed face (3) having perforations (4) therein to help lock the veneer (not shown) in place. The formed face (3) is most preferably high energy phosphatized before bonding the veneer in place.

Figure 2:
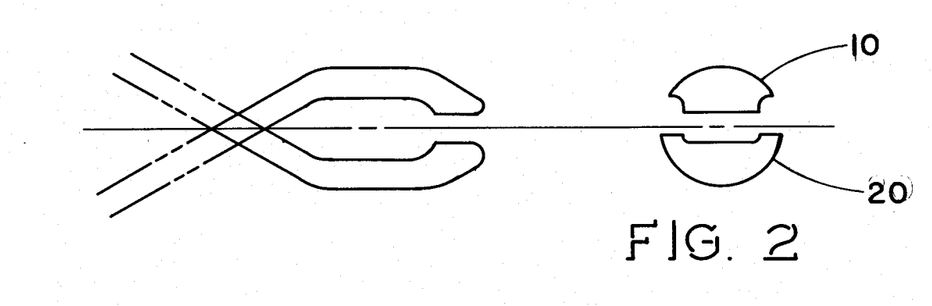
FIGS. 2 and 2A show two embodiments of dies suitable for forming the formed face in a dental crown substrate.
Figure 2A:
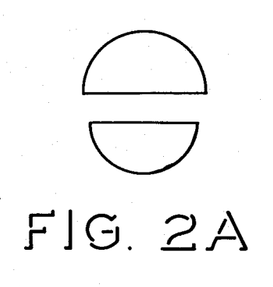

FIGS. 2 and 2A show two different suitable sets of dies, one half of each set being male (10) and the other half of each set being female (20) in plan view, for forming the formed face in a dental crown. These die sets may be used in any suitable type of compression applying means, such as, for example, pliers-like tools or arbor type presses.

Figure 3:
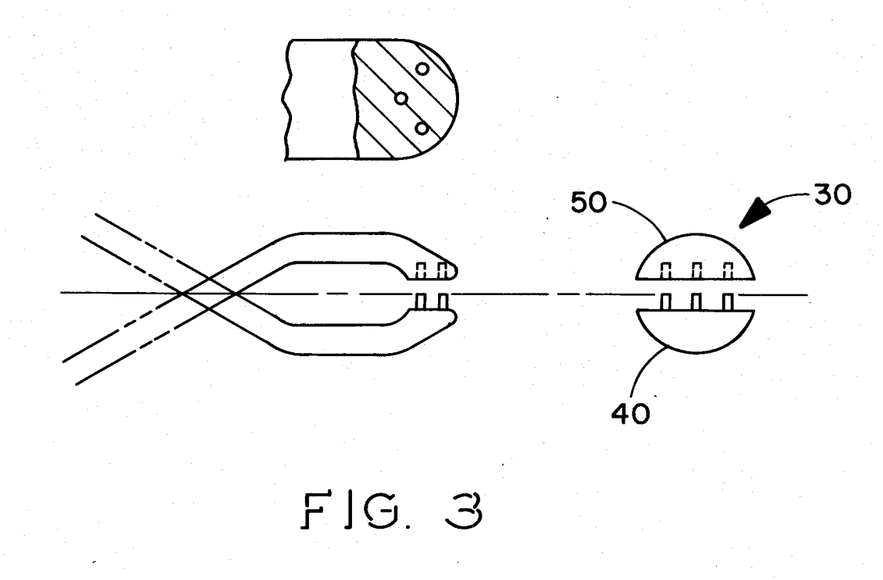
FIG. 3 shows a perforating die suitable for use in making the perforations in said formed face.

FIG. 3 shows a die set (30) having a male half (40) and a female half (50) suitable for use in a compression applying means for forming the perforations in the formed face to help lock the veneer in place. Again a hand pliers-type of compressive means or arbor-type of pressing means is suitable.

Figure 4:
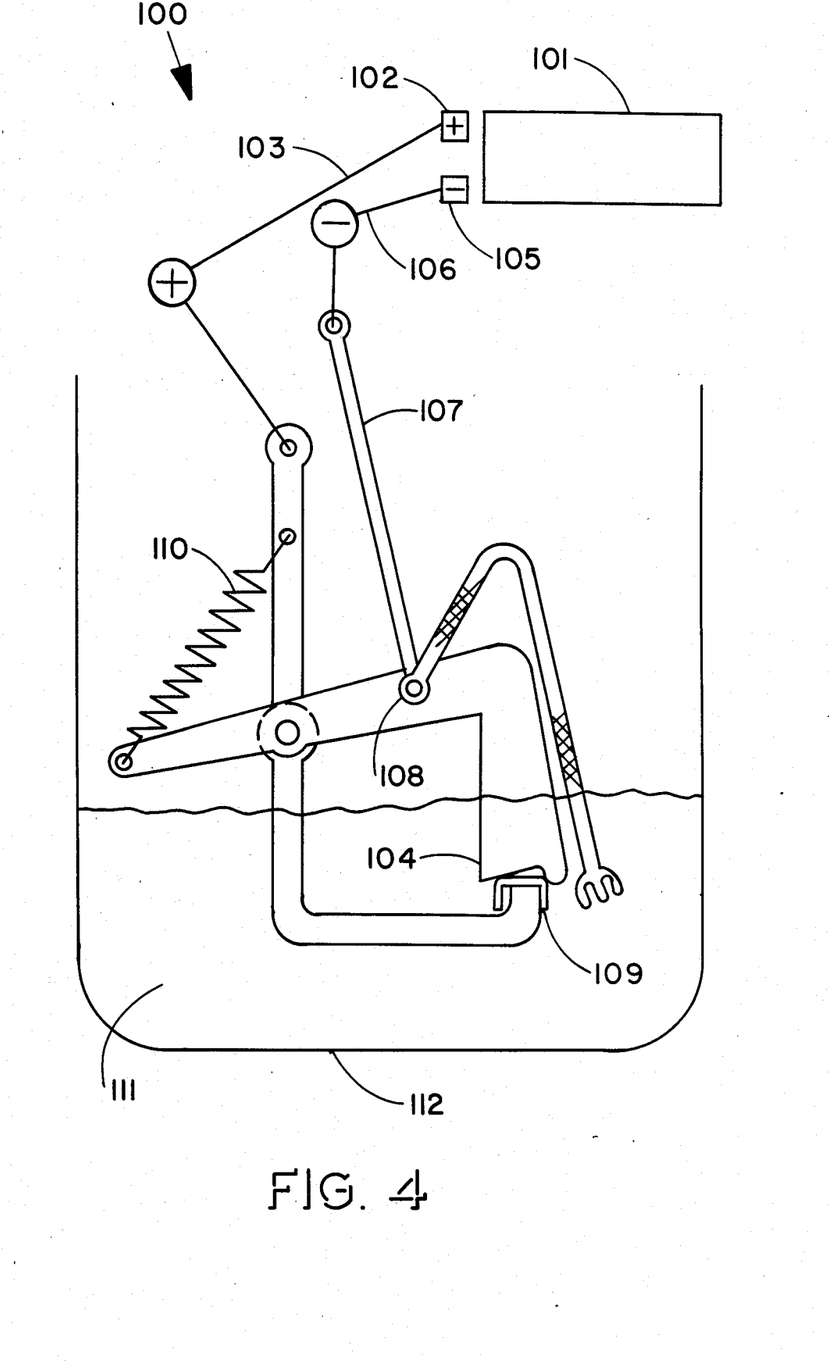
FIG. 4 shows one embodiment of an electrolytic cell suitable for phosphate etching the formed face of a dental crown substrate.

FIG. 4 shows a schematic of an electrolytic cell (100) suitable for use in this invention. This cell has a DC power source (101) a positive electrode (anode) (102) connected to the positive side of the DC power source (101) by wire (103). Said positive electrode (102) has a preformed dental crown holding and registering section (104). A negative terminal (105) is connected to the negative side of the DC power source (101) by wire (106) and to a suitable ground by ground strap (107). Said negative electrode (cathode) is insulated from and movably attached to the positive electrode at point (108) and the preformed dental crown (109) is clamped in place through pressure applied by spring (110). Electrolyte (111) fills the container (112) where it princi-
pally serves as the etching media. Because of the design of the electrodes only the area of the formed face will be etched. This means that a masking step is not necessary when utilizing this system. The benefit is that the areas of the dental crown which will not be veneered will retain their smoothness and prevent patient irritation that would be caused by a roughened exposed surface.

Figure 5:
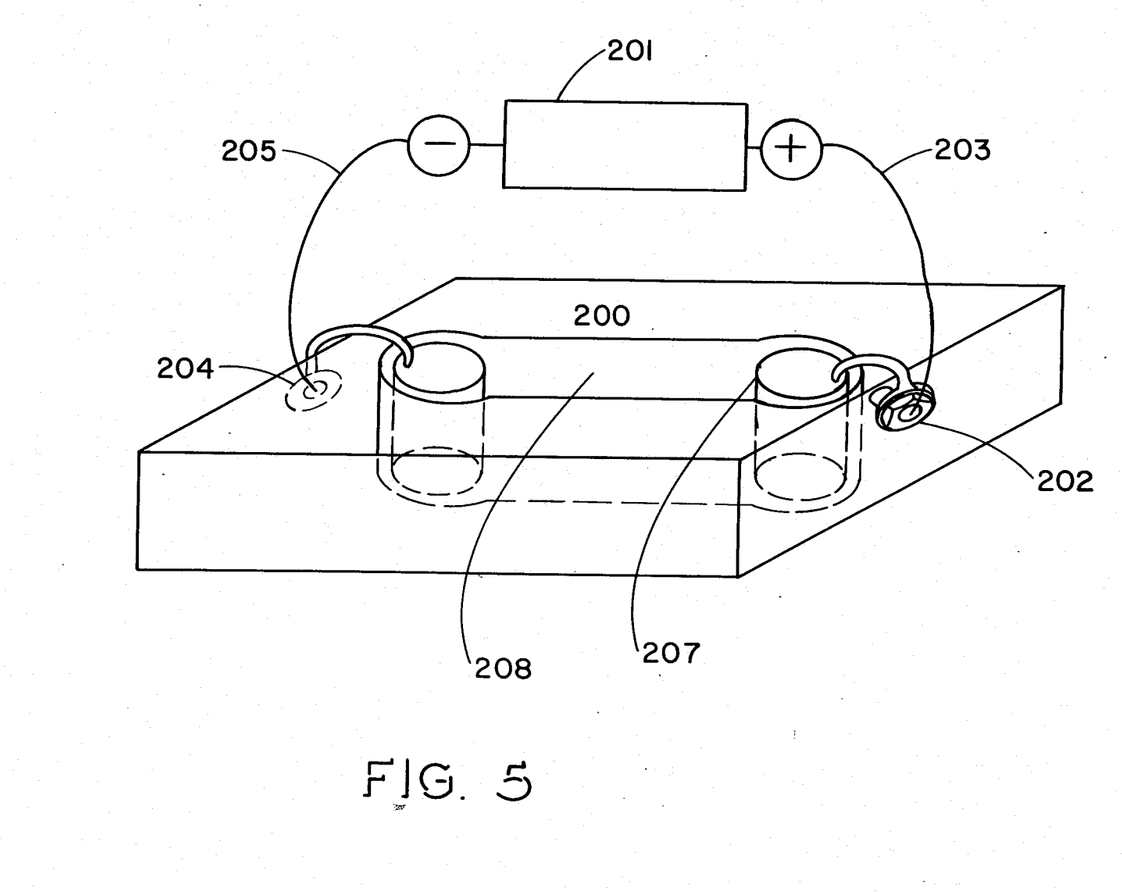
FIG. 5 shows an embodiment of a thermoelectrolytic cell suitable for phosphate etching and high energy phosphatizing the formed face of dental crown substrates.

FIG. 5 shows a schematic of a preferred thermal electrolytic cell configuration suitable for use in the present invention. This cell (200) has a DC power source (201) a positive electrode area clamping means (202) connected to the positive side of said DC power source by wire (203) and a negative electrode area and clamping means (204) connected to the negative side of the DC power source by wire (205), said clamping means (202) and (204) being fixedly attached to cell body (200), said cell body having a preformed face dental crown (207) electrolytically connected by a high energy cell passage (208) and containing electrolyte therein to transmit the ions to a second dental crown serving as the cathode.

DETAILED DESCRIPTION OF THE INVENTION

In accordance with this invention, a substrate such as a dental crown is provided having a surface cleaned of grease and other surface contaminants. Suitable substrate materials include metals, approved high strength dental alloys and stainless steel alloy substances. Surface preparation and cleaning may be accomplished by a variety of methods known in the art, for example, detergent baths, acid or caustic baths, ultrasonic vibration baths, and alcohol washes. All of the above-mentioned methods would be acceptable for cleaning the dental crown substrate before it is placed in a patient's mouth. It is realized that in the case of cleaning the substrate material while it is actually in the patient's mouth for purposes of post installation repairs, will necessitate that certain cleaning procedures would be amenable while others would not. In some cases a dental crown, which has already been installed by the normal procedure, may be roughened by a dental grinding tool, holes drilled, degreased with ethyl alcohol, phosphatized by wiping with a phosphoric acid solution and the coating applied after rinsing and drying. This is not a preferred approach, however, because maximum adhesion is not offered.

Further in accordance with the preferred embodiments, the substrate surface is coated with a phosphate coating by electroetching. It is to be understood that while the phosphate etching step produces the preferred embodiment, an acceptable dental crown composite can be produced without the phosphate coating being produced during the etching step. Suitable phosphate etching electrolytes include, for example, phosphoric acid solutions, phosphoric acid solution containing peroxides (hydrogen peroxide), phosphoric acid solutions containing hydrochloric acid, phosphoric acid solutions containing sulfuric acid, or acetic acid or nitric acid. Suitable non-phosphate containing etching electrolytes are, for example, sulfuric acid solutions, hydrochloric acid solutions, combinations of acid solutions including nitric and acetic acid.

Further in accordance with the invention, a veneer coating of an acrylic or other dental approved polymeric material is bonded to the dental crown substrate. In the preferred embodiments this veneer coating of organic polymeric material is chemically bonded to the phosphate layer which has been electrochemically deposited upon the dental crown substrate prior to the veneering step. While this resin coating material may be applied by methods generally understood in the art of polymeric coatings, in the preferred embodiments, the polymeric veneer comprises applying a primer coating layer of a desired thickness, curing said primer coating using a curing means, applying a bonding coat of a desired thickness on said cured primer coating, and curing said bonding coat layer by a curing means. Suitable curing means include photocuring, thermal curing, microwave curing, and other energy curing practices common to the coating industry. Suitable coating materials include, for example, acrylics, epoxies, polyesters or other dental approved polymeric resin coatings. Preferred coating materials are made by the L. D. Caulk Company, Milford, Delaware, such as Prisma Fil, Silux made by the 3M Company or Durafill made by Kulzer Company.

Further in accordance with this invention is provided a method for installing the dental crown composites of this invention. The preferred method comprises surgically stabilizing the tooth to receive the dental crown composite, shaping the tooth stub of the tooth which has been stabilized, selecting the proper size dental crown substrate, forming the formed face in said dental crown substrate, shaping said dental crown substrate to fit the tooth stub and the mouth, degreasing and electro-etching said formed face of said dental crown substrate, applying the polymeric coating material veneer to said formed face of said dental crown substrate thereby creating a polymeric coating veneered dental crown composite, fitting to said tooth stub and cementing said dental crown composite to said shaped tooth stub.

The basic precepts for installing dental crowns is well established and may be found, for example, in such basic texts as "Theory and Practice of Crown and Fixed Partial Prosthodontics (Bridges)", S. Tylman, the C. V. Mosby Company, Sixth Edition (1970), which is hereby incorporated by reference. A second reference which specifically describes the stainless steel cap procedure is "Dentistry for the Child and Adolescent", Ralph C. McDonald, the C. V. Mosby Company, pp. 206-209 (1974) which is also herein incorporated by reference.

In the preferred embodiment of this process, the electroetching step comprises degreasing the formed face of the dental crown substrate, etching said degreased formed face using an electroetching means, and rinsing and drying the electroetched dental crown composite of the previous step using a rinsing means and a drying means. Further, the electroetching is carried out in a phosphate containing electrolyte in the most preferred embodiment. Suitable degreasing agents have been listed hereinabove and suitable etching electrolytes comprise solutions containing peroxides, sulfuric acids, acetic and nitric acids. Suitable electrolytes containing phosphate ions producing a phosphate layer on the etched dental crown substrate include phosphoric acid solutions containing peroxides and/or sulfuric acids, hydrochloric acid, acetic acid and nitric acid.

Methods of rinsing and drying electrolytically etched and/or phosphatized materials are generally suitable for use in the present invention. The method presently preferred by the inventors for rinsing and drying is by water rinsing and blowing air across the treated surface.

Suitable electrolytic cells are well understood in the art. The only criteria that is required is that a good etching is produced on the surface, and in the case of a phosphate coating, a good phosphate coating is provided of the desired thickness. Additionally, for the presently preferred embodiments of electrolytic cells, refer to FIGS. 4 and 5 showing two forms of suitable electrolytic cells for use with the present invention.

High energy phosphatizing is a unique feature of the apparatus of FIG. 5. This is due to the high energy at the substrate interface which results from the ion transfer in this low volume cell. The heat in this cell rises to 170°-200° F. in 20 to 200 seconds depending on the voltages.

The electro-chemical treatment described shows an apparatus, FIG. 4, which allows simple placement of a dental crown over the anode contact. This apparatus is complete with the cathode. The entire apparatus with dental crown is inserted into a small container (beaker) of the formulated electrolyte and the direct current is applied (approximately 2 Amps). In this case it requires several minutes to etch and treat.

This procedure provides a cleaning effect from oxygen gas scrubbing, etching for increased surface area with simultaneous formation of a phosphatized film for improved coating bonding. As hereinabove and hereafter used, this is what Applicants are describing when utilizing the term phosphatize. Electro-polishing is well known in the metal finishing industry and normally high concentrations of phosphoric acid are used for ferrous alloys. The anode reaction can include the following reactions.

$Fe + X\ H_2O \rightarrow Fe^{+2} + 2e^-$ $H_2O + Acid \rightarrow \frac{1}{2}O_2 + H^+$ The cathode reaction:

$H_2O \rightarrow H_2 + \text{reduction effects}$

Because of the shape and placement of the cathode with respect to the face of the dental crown (anode) only the preferred register area is etched and treated.

Etching is achieved by oxidation of the metal and subsequent solubility in the electrolytic solution.

The preferred solution is a 40% part by weight solution of phosphoric acid and one percent by weight of a 3% solution of hydrogen peroxide.

Anode Mechanisms and Phosphatizing Formation of $O_2$

During this reaction because of oxygen over voltage, oxygen gas is being formed.

If the substrate is stainless steel, the solubilizing of other metals of this alloy also occurs in a similar manner. Hydrogen peroxide is added to prevent formulation of phosgene at the cathode.

Reactions at the anode, because of the use of phosphoric acid, promotes phosphatizing.

Normal phosphatizing shows the reaction $Fe° + 2H_3PO_4 \rightarrow Fe(H_2PO_4)_2 + H_2$ which may be described in a general equation where M=the metal as:

$M(H_2PO_4) \rightarrow M(HPO_4) + H_3PO_4$ $3M\ (H_2PO_4) \rightarrow M_3(PO_4) + 4H_3PO_4$ $3M(HPO_4) \rightarrow M_3(PO_4) + H_3PO_4$ In these equations, the equilibrium shifts from the right to the left because of precipitation of the sparingly soluble secondary and tertiary phosphates. Acid is consumed at the substrate surface. The precipitated compound attaches to the surface of the clean metal with a highly interlocked crystalline layer. This layer which is relatively thick improves coating adhesion because it is porous. Phosphorous compounds have a number of hydroxyl groups known to promote the high adhesive strength from hydrogen bonding with the molecules of the applied film.

FIG. 5 describes the preferred configuration for holding the dental crown which reduces the electrolyte volume to a few cubic centimeters or less.

On applying a current of about ½ to 5 AMPs, the cell electrolyzes actively. Etching occurs rapidly as the electro and thermal energy is concentrated in a very small volume. The electrolytic solution heats quickly from ambient to a temperature in the range of from 70° to 90° Centigrade. After a short 2 minute cycle or less, the cell is rinsed and the desired anode serving dental crown or similarly shaped metal apparatus is removed, dried, coated and inserted according to the practice of this application.

Etching may be carried out either before or after crown fitting. The preferred practice is that a cleaner surface is offered from the approach of cleaning and etching after proper fitting.

It is a feature of this invention that allows the dentist practicing this art to have the flexibility to choose the best process sequence for the specific application.

The chemistry of the electrolytic cell of FIG. 5 is unique and offers many theoretical explanations for improved adhesion. While not prescribing to any particular theory of operation, the following is offered solely as illustrative of possible theoretical models. Because the electrolytic process is occurring rapidly and at a high temperature, with very high surface energy, it can be theorized that the metal phosphate formed compounds may be attached to metal atoms of the substrate at one of their valence sites. The remaining portion of these metal atoms will be still contained in the crystal structure of the substrate.

Also, the bonded metallic phosphorous oxygen compounds may be of variety of configurations and attached to the substrate by either one or two valence bonds.

The producing of the formed face and the production of perforations within the formed face area may be achieved by any suitable, recognized means within that particular art. One of the preferred modes of providing the formed face and the perforations if used is by use of a hand compression-type tool, i.e. pliers-like apparatus, having the appropriate dies incorporated in the head thereof. One's attention is drawn to FIGS. 2 and 2A which show two particularly preferred embodiments of dies suitable to produce the formed face and FIG. 3 which shows a particularly preferred die for producing the perforations within the formed face area. It should also be noted that arbor-type presses are suitable and in many cases preferred means for forming both the formed face and the perforations in the dental crown. It is possible to achieve these desired retention holes by drilling.

It is also apparent to those skilled in the art of veneering metal substrates with polymeric coatings that once the metal or organic film bond has been achieved it can serve as an intermediate layer for subsequent adhesive lamination of other aesthetic films such as mylar, ceramics, porcelain, and other glasses.

To further illustrate the invention, Applicants have performed laboratory experiments which have yielded excellent results in providing a structurally sound and durable veneer composite. The examples which follow, which should not be considered as limiting the invention but rather only as exemplary of various embodiments, are based on those laboratory results.

A test program was carried out to determine strength of the bond using various treatments.

EXAMPLE 1

Bonding to Chrome Alloy Biobond II

The chrome alloy Biobond II manufactured by the Dentsply/York Division, Dentsply International Inc., York, P.A. was used to prepare a cast Laboratory dental crown which was used as a substrate to which primer (L.T.D. Caulk Company Prisma fill primer) was bonded after the crown had been etched by the laboratory by wipe application and light curing (Wite-Lite manufactured by Phase Alloy, Inc. was applied). The veneer was applied using the L. D. Caulk Company Prisma fill and light cured for 60 seconds.

A dental pick was wedged between the coating and the substrate. This caused the veneer to be chipped away only in the immediate area of the coating where the dental pick was wedged. This was viewed as an excellent bond as opposed to one where the application of the dental pick being wedged between the coating and the substrate caused the coating to "pop" off in a single piece or several large pieces covering an area greater than that over which the mechanical pressure was applied.

EXAMPLE 2

Bonding to Stainless as the Substrate (Comparative Example)

A dental crown made from 304 stainless steel was wiped clean with ethyl alcohol to remove the greaselike substances and the veneer bonded as described in Example 1. When tested as in Example 1, the coating failed by "popping off" as the wedge pick penetrated the bond interface. Poor adhesion was observed.

EXAMPLE 3

Bonding to Acid Etched Stainless Steel (Standard Etching of Whole Crown)

A 304 stainless steel dental crown was etched by having been:

(a) degreased with alcohol, (b) etched in a hot (170° to 190° F.) solution of 40% parts by weight sulfuric acid for 10 minutes, (c) rinsed and etched in a hot solution (170° to 190°) of hydrochloric acid for 1 minute and rinsed, (d) phosphatized in a phosphoric acid 15% parts by weight solution for 10 minutes at room temperature, (e) rinsed and dried, and veneer bonded as in Example 2 (Microscopic observation of this surface showed a rough surface with the metal crystals showing over the total surface area of the dental crown and not just in the area of the formed face).

Using the pick wedge test, the coating bond was determined to be good. This approach provides a marginally suitable bond but to be used requires a mask coating over the dental crown when etching to preserve the smoothness of the non-formed face area.

A dental crown prepared in this manner, etched with masking to preserve the smoothness of the non-veneered area to prevent a rough surface irritation in the patient's mouth after fitting, was veneered and installed in a male mouth at tooth number 12. It has been in service for over 12 months without a sign of failure.

EXAMPLE 4

Bonding In Situ to a Stainless Steel Dental Crown

A stainless steel dental crown that had previously been installed in a male's mouth in tooth number 5 was roughened with a diamond burr (a dental grinding tool) and drilled with a 33⅓ inverted cone carbide burr according to the geometry of FIG. 1. It was wiped with ethyl alcohol to degrease the surface and a 40% solution of phosphoric acid was applied to this surface for 1 minute. The veneer coating was applied as in EXAMPLE 1. There has been no failure observed after over 9 months of service.

EXAMPLE 5

Bonding to a Formed Face Phosphatized Stainless Steel Dental Crown

A stainless steel dental crown had a formed face and holes prepared as in FIG. 1. It was degreased and etched and phosphatized as in EXAMPLE 3.

The veneer was applied as in EXAMPLE 1. The coating bond was excellent. It broke from the qualitative pick wedge test but did not pop off.

A stainless steel dental crown which had a formed face and holes prepared, as described in this example, was fitted to a female at tooth number 18. After fitting it was masked, etched and phosphatized as in EXAMPLE 3. It was veneered as in EXAMPLE 1 and installed.

It has been in service for over 10 months without signs of failure.

EXAMPLE 6

Bonding to an Electrolytically Etched Stainless Steel Dental Crown

A stainless steel dental crown had a formed face and holes prepared as in FIG. 1. It was placed in a fixture and cell similar to that of FIG. 4 with a 40% parts by weight phosphoric acid solution. After a DC voltage of 5 volts and approximately 0.1 amps was applied for 10 minutes, the so prepared crown was rinsed and dried. A veneer coating was applied as in EXAMPLE 1. The bond strength of the coating, using the dental pick wedge test, was good. Microscopic observation showed a light etch and the crystal structure of the metal only in the formed face area.

EXAMPLE 7

Bonding to an Electrolytically Etched Formed Face Stainless Steel Dental Crown

The same procedure as EXAMPLE 6 was followed with a formed stainless steel crown which had a hole configuration similar to FIG. 1.

The results from the wedge test were excellent.

EXAMPLE 8

Bonding to a Thermal Electrolytically Etched Phosphatized Dental Crown

Two stainless steel dental crowns without formed faces or holes were degreased and placed in a fixture similar to FIG. 5. A 40% parts by weight solution of phosphoric acid which contained 1% of hydrogen peroxide was poured into the cell.

A current of 0.8 amps was applied for 1 minute and the dental crown of the negative electrode was removed by rinsing, pouring out all of the electrolyte which had reached a temperature of 190°, further rinsed with water, and air dried. A veneer coating was applied as in EXAMPLE 2.

Microscopic examination showed the surface of the substrate to have a light etch. The crystal structure of the metal could clearly be observed in this isolated face area. This clearly illustrates that only the area to be veneered is roughened by etching.

The adhesive bond using the wedge test was excellent.

EXAMPLE 9

Bonding to a Thermal Electrolytically Etched Phosphatized Formed Dental Crown

A stainless steel dental crown formed as shown in FIG. 1 was treated as described in EXAMPLE 8.

The bond strength was excellent and superior to the product of EXAMPLE 8. These were the best qualitative results of all the examples.

EXAMPLE 10

Patient Application of a Veneered Dental Crown Procedure as in EXAMPLE 9

After the tooth (No. 4) stub was shaped in a female mouth, a suitable formed face dental crown with holes as in FIG. 1 was fitted. The dental crown was degreased and treated as in EXAMPLE 9. The dental crown was installed and has been in service for over 9 months without any signs of failure.

EXAMPLE 11

The procedure of EXAMPLE 10 was repeated with another female patient's tooth number 12.

This tooth has been in service for over 9 months without any sign of failure.

Although the invention has been described in terms of particular embodiments including these which Applicants believe to represent the best modes of the invention at the time of this application, it will be recognized by those skilled in the art that various changes may be made in the composition and method embodiments of this specification without departing from the scope of the invention as defined in the following claims.

What is claimed is:

1. A dental crown composite comprising:
   (a) a stainless steel dental crown substrate having a recessed formed face suitable for retaining a veneer coating, and
   (b) a veneer coating of an acrylic material chemically bonded to said stainless steel dental crown substrate in said recessed formed face.

2. A dental crown composite as claimed in claim 1, wherein said formed face has perforations therein.

3. A dental crown composite as claimed in claim 1, wherein said composite is adhesion laminated with at least one additional aesthetic film of mylar.

4. A dental crown composite as claimed in claim 1, wherein said composite is adhesion laminated with at least one additional aesthetic film of ceramic.

5. A dental crown composite as claimed in claim 1, wherein said composite is adhesion laminated with at least one additional aesthetic film of porcelain.

6. A dental crown composite as claimed in claim 1, wherein said composite is adhesion laminated with at least one additional aesthetic film of a glass.

7. A dental crown composite comprising:
 (a) a stainless steel dental crown substrate having a recessed formed face suitable for retaining a veneer coating,
 (b) a phosphate layer applied to a desired thickness to the surface of said recessed formed face of said substrate, and
 (c) a veneer coating of an acrylic material chemically bonded to said phosphate layer on said stainless steel substrate in said recessed formed face.

8. A dental crown composite as claimed in claim 7, wherein said formed face has perforations therein.

9. A fixed prosthetic method for installing the dental crown composite comprising:
 (a) surgically stabilizing the tooth receiving the dental crown,
 (b) shaping the tooth stub,
 (c) selecting the proper size stainless steel dental crown substrate,
 (d) forming a recessed formed face in said stainless steel dental crown substrate of step (c),
 (e) shaping said stainless steel dental crown substrate of step (d) to fit the tooth stub of step (b) and the mouth containing said tooth stub,
 (f) electro-etching said recessed formed face of said stainless steel dental corwn substrate,
 (g) applying and chemically bonding an acrylic material veneer to said recessed formed face of said stainless steel dental crown substrate, thereby creating an acrylic veneered stainless steel dental corwn composite fitting said tooth stub of step (b), and
 (h) cementing said stainless steel dental crown composite of step (g) to said shaped tooth stub of step (b).

10. A fixed prosthetic method as claimed in claim 9, wherein said electro-etching of step (f) comprises:
 (a) degreasing the recessed formed face of the stainless steel dental crown substrate,
 (b) etching said degreased recessed formed face using an electro-etching means,
 (c) rinsing and drying the electro-etched stainless steel dental corwn substrate of step (f) using a rinsing and a drying means.

11. A fixed prosthetic method as claimed in claim 9, wherein said application of said acrylic material comprises:
 (a) applying a primer coating layer of the desired thickness,
 (b) curing said primer coating using a curing means,
 (c) applying a bonding coat layer of a desired thickness on said cured primer coating, and
 (d) curing said bonding coat layer by a curing means.

12. A fixed prosthetic method as claimed in claim 11, wherein said curing means of steps (b) and (d) is photo-curing.

13. A fixed prosthetic method as claimed in claim 12, wherein said die forming means is an arbor press.

14. A fixed prosthetic method as claimed in claim 11, wherein said curing means of steps (b) and (d) is heat curing.

15. A fixed prosthetic method as claimed in claim 11, wherein said curing means of steps (b) and (d) is chemical curing.

16. A fixed prosthetic method as claimed in claim 9, wherein said forming of said formed face of step (d) utilizes a die forming means.

17. A fixed prosthetic method as as claimed in claim 16, wherein said die forming means comprises a die activated by a hand compressing means.

18. A fixed prosthetic method as claimed in claim 9, wherein said step (d) also comprises perforating said formed face using a perforating means.

19. A fixed prosthetic method as claimed in claim 18, wherein said perforating means is activated by a hand compressing means.

20. An in situ method of veneering a previously installed stainless steel dental crown comprising:
 (a) roughening said previously installed stainless steel dental crown with a dental grinding means,
 (b) forming a recessed formed face area utilizing a dental drilling means,
 (c) degreasing said recessed formed face,
 (d) etching said recessed formed face with an etching solution,
 (e) rinsing and drying said etched recessed formed face, and
 (f) applying and chemically bonding an acrylic material veneer in said recessed formed face.

* * * * *